(12) United States Patent
Wendlandt et al.

(10) Patent No.: US 6,554,820 B1
(45) Date of Patent: *Apr. 29, 2003

(54) COMPOSITE FLEXIBLE TUBE FOR MEDICAL APPLICATIONS

(75) Inventors: Jeffrey Michael Wendlandt, Newton, MA (US); Yem Chin, Burlington, MA (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/521,625

(22) Filed: Mar. 8, 2000

(51) Int. Cl.[7] ............................................. A61M 25/00
(52) U.S. Cl. ................................................... 604/527
(58) Field of Search ................... 604/523, 524, 604/525, 526, 527; 600/139–144, 145; 138/123–127, 129–134, 137, 138, 140, 144, 172, 174; 87/2, 7, 8, 9

(56) References Cited

U.S. PATENT DOCUMENTS

| 4,676,228 A | 6/1987 | Krasner et al. |
| 4,981,478 A | 1/1991 | Evard et al. |
| 5,057,092 A | 10/1991 | Webster, Jr. |
| 5,243,967 A | 9/1993 | Hibino |
| 5,554,139 A | 9/1996 | Okajima |
| 5,782,811 A * | 7/1998 | Samson et al. ............ 604/282 |
| 5,951,539 A | 9/1999 | Nita et al. |
| 6,206,824 B1 * | 3/2001 | Ohara et al. ................ 600/139 |

FOREIGN PATENT DOCUMENTS

| JP | 2000-309 | 1/2000 | .......... A61M/25/00 |

* cited by examiner

Primary Examiner—Michael J. Hayes
(74) Attorney, Agent, or Firm—Kenyon & Kenyon

(57) ABSTRACT

A flexible composite tube for medical applications is described. The tube has the ability to transmit a torque and to resist compression, tension, and kinking. The tube is also very flexible in bending, and has a small wall thickness. Different layers are used to obtain the desired properties. Torsional stiffness is obtained by embedding a braid in an elastomeric material. Resistance to kinks and to compression and tension is obtained by placing coils radially inward or outward of the braid. Smooth plastic layers are used to seal the assembly, and facilitate sliding in a body cavity.

3 Claims, 3 Drawing Sheets

COMPOSITE FLEXIBLE TUBE FOR MEDICAL APPLICATIONS

The present invention is related to a composite flexible and kink-resistant tube that can be used for medical applications. In particular, the composite tube is capable of transmitting a torque, and of opposing tension and compression forces.

DESCRIPTION OF RELATED ART

Modern medical procedures make extensive use of a variety of hollow tubes that are inserted in a patient's body, especially in connection with various non surgical procedures. These procedures are performed to visually inspect the inside of various body cavities, and to remove tissue samples, as well as diseased tissues. This is done without having to cut thorough the patient's skin and muscles to reach the desired location within a body cavity.

Some examples of the tools used for these procedures include endoscopes, full thickness resectioning devices (FTRD) used to remove large tissue samples from inside the intestine, devices to treat gastro-esophageal reflux disease (GERD), and various catheters. In addition, tubes with a much smaller diameter are used to inspect and to deliver compounds and devices to the vascular system.

The tubes used in these applications typically define a working channel bound by the tube, through which medical devices can be easily introduced in the body cavity, and must meet several requirements. The tubes must be flexible, so that they can follow the shape of the intestine, the esophagus, or of other body cavities without damaging the surrounding tissue, and in some cases without excessive discomfort to the patient. In many cases, the tubes must be capable of resisting stretching under tension, collapsing under compression, or both. This is especially important in endoscopes, that generally have to be pushed through the intestine from outside the body. These medical tubes also must be kink resistant, so that they will not easily jam inside the body cavity, and so that their cross sectional area remains constant. This is important so that other medical devices can be inserted through the tubes without binding. For many applications it is also important that the tube transfer a torque applied to one end of the tube to the other end. For example, this ability is useful to rotate a vision device mounted on the far end of an endoscope, by rotating the near end.

Medical tubes have been constructed that attempt to combine these required characteristics using coils or braids as structural elements. However, the current tubes are generally of small diameter, and are not suitable for use in the digestive tract. When made of a larger diameter, the tubes have an excessively thick wall, which increases their bending stiffness and reduces the size of the working channel through which additional tools can be introduced.

In view of the foregoing, there is a need for a composite tube for medical applications that is flexible and has a thin wall, while also resisting kinking, transmitting torque, and resisting deformation while under tension or compression.

SUMMARY OF THE INVENTION

The present invention is directed to a composite tube for medical applications that substantially obviates one or more of the problems due to limitations and disadvantages of the related art.

Additional features of the invention will be set forth in the description which follows, and in part will be apparent from the description, or may be learned by practice of the invention. The objectives and other advantages of the invention will be realized and attained by the apparatus and method particularly pointed out in the written description and claims hereof, as well as the appended drawings.

To achieve these and other advantages and in accordance with the purpose of the invention, as embodied and broadly described, the invention is a flexible composite tube for medical applications having a longitudinal axis, that comprises a tubular braid adapted to transfer a torque along the longitudinal axis, the tubular braid being made of intertwined wire elements, a coil disposed longitudinally along the tube, adapted to limit radial movement of the tubular braid, and a tube-like elastic layer, disposed adjacent the tubular braid, forming a composite element with the tubular braid to restrict relative movement of the wire elements.

In another embodiment, the invention is a flexible composite tube for medical applications, that has a tubular braid made of intertwined wire elements adapted to transfer a torque along a longitudinal axis of the tube, an inner coil disposed longitudinally along the tube, radially inside of the tubular braid, adapted to limit radial contraction of the tubular braid, and an outer coil disposed longitudinally along the tube, radially outside of the tubular braid, adapted to limit radial expansion of the tubular braid.

In yet another embodiment, the invention is a flexible composite tube for medical applications having a longitudinal axis, and having an inner tubular braid disposed along the longitudinal axis, an outer tubular braid disposed radially outside of the inner tubular braid, said inner and outer tubular braids being adapted to transfer a torque along a longitudinal axis of the tube, and being made of intertwined wire elements. The tube has a coil disposed longitudinally along the tube, radially inside of the outer tubular braid and radially outside the inner tubular braid, adapted to limit radial contraction of the outer tubular braid and radial expansion of the inner tubular braid.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention, are incorporated in and constitute a part of this specification, illustrate embodiments of the invention and, together with the description, serve to explain the objects, advantages, and principles of the invention. In the drawings.

DETAILED DESCRIPTION OF PREFERRED EMBODIMENTS OF THE INVENTION

Medical tubes used in endoscopes and in similar devices have to be as flexible as possible, while meeting certain structural requirements, and retaining a wall that is as thin as possible. These sometimes contradictory requirements can be met by forming the tube from separate structures that cooperate together to give the tube its desired properties. These tubes are referred to as composite tubes.

Figure 1:
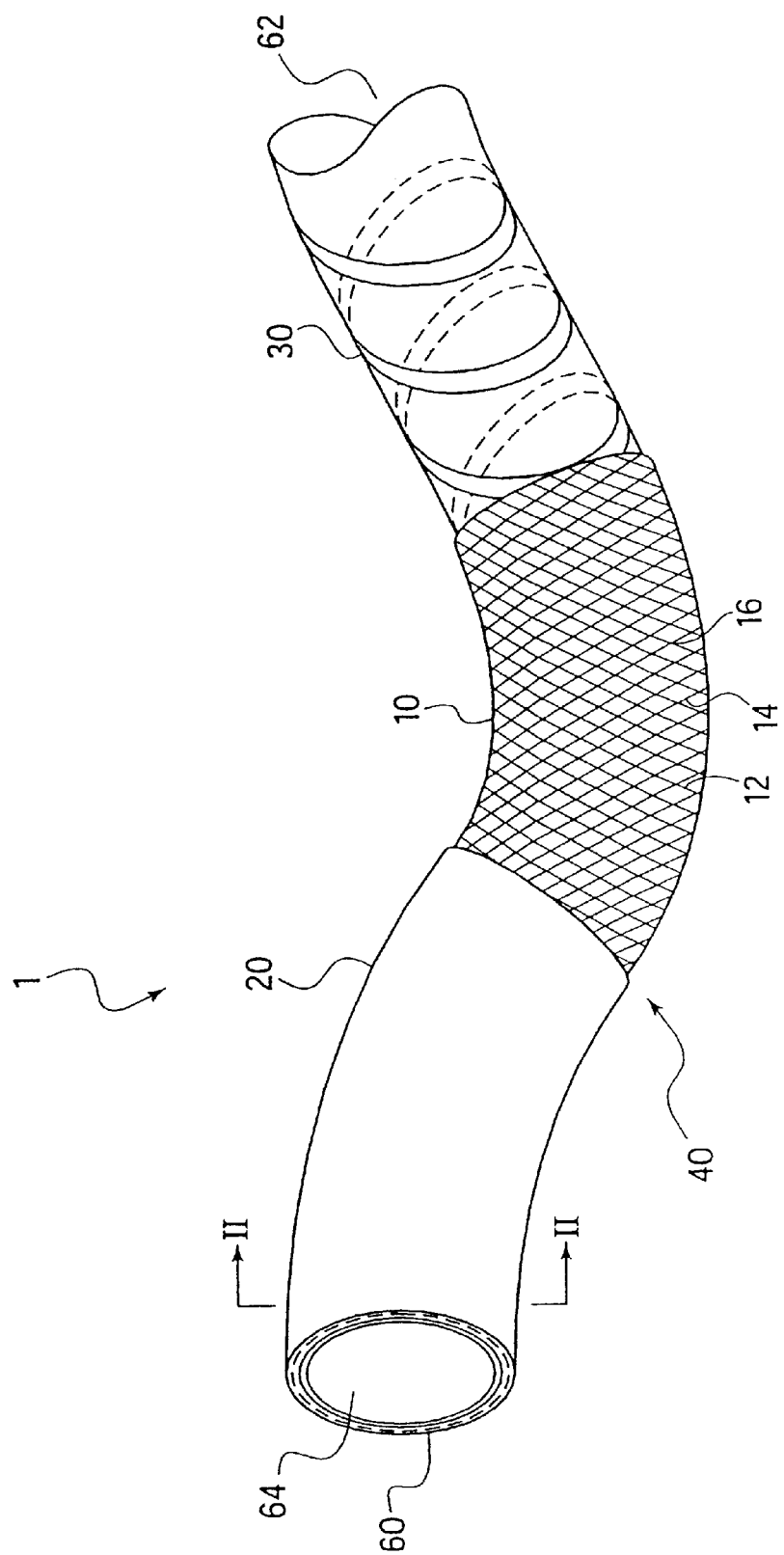
FIG. 1 is a schematic view showing the several layers of one embodiment of a composite medical tube according to the invention.

FIG. 1 shows a composite tube 1, that is formed by combining a braid 10, an elastomeric layer 20, and a coil 30. As will be explained later, the braid 10 is preferably fully embedded in the elastomeric material 20. The coil 30, on the other hand, can be fully or partially embedded in elastomeric material 20, or can be a free coil placed adjacent to the braid 10. The combination of braid 10 embedded in elastomeric material 20 forms a composite element 40.

Braid 10 is used principally to form a structural frame for the tube, and to transmit a torque along the length of tube 1. For example, if remote end 60 of tube 1 has to be rotated along its axis, near end 62 can be twisted so that the twisting motion is carried by braid 10 all the way to remote end 60. This feature is particularly useful when additional medical tools such as cutting instruments and vision devices are placed in working channel 64 of tube 1, and have to be rotated to a desired position in the body cavity. Accordingly, braid 10 is tube-shaped, having a surface that extends as an undivided, substantially continuous tube or sheath without interruption along the longitudinal axis.

In addition to increasing the torsional stiffness of the tube 1, braid 10 also couples linear movement along the axis of the tube to radial movement of the tube walls. Accordingly, when the braid is compressed, its length tends to decrease, while its diameter tends to increase. Conversely, when braid 10 is stretched under tension, its length increases, and its diameter tends to be reduced. This property of the braid makes it possible to control the axial deformation of the braid, as will be fully explained below.

Braid 10 is generally formed in a known manner by intertwining two or more wires to form a tubular mesh. In a preferred embodiment, the wires are metal wires made of stainless steel. For example, wires 12 running in one direction, and wires 14 running at an angle to wires 12 criss-cross at points 16. The two sets of wires can rotate and slide past one another at points 16, so that the entire braid 10 rotates about the longitudinal axis as a unit. When braid 10 changes length, the links formed by wires 12 and 14 can be stretched and contracted in an accordion-like movement.

Figure 2:
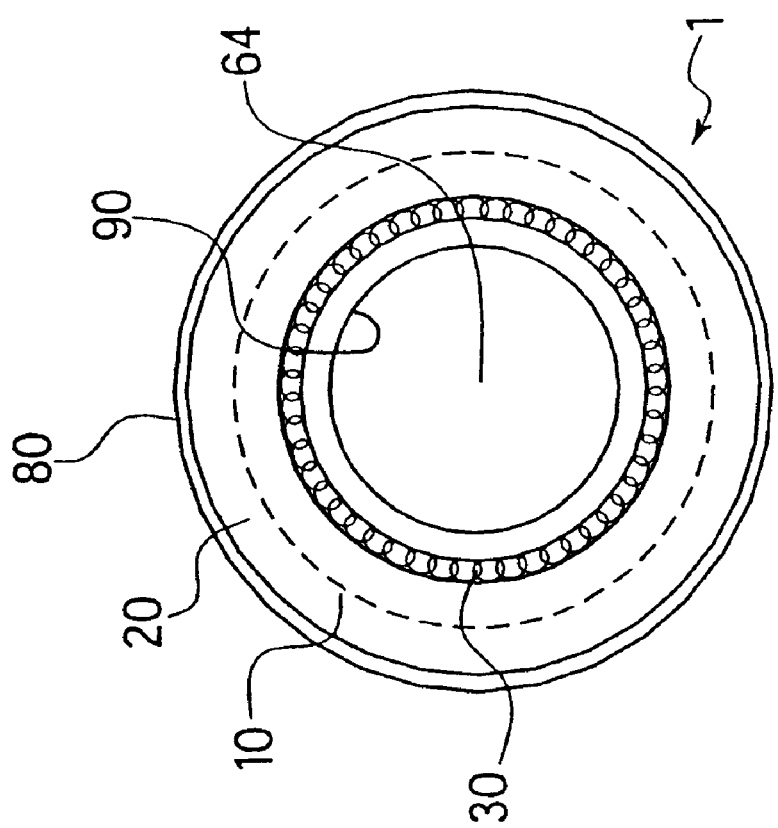
FIG. 2 is a cross section on line II—II of FIG. 1, showing a composite tube with one braid and one coil.

In a preferred embodiment, braid 10 is embedded in elastomeric layer 20. Preferably braid 10 is completely embedded in the elastomer, however it can also be partially embedded in elastomeric layer 20, so that only one surface of braid 10 is attached to the elastomer. The purpose of elastomeric layer 20 is to tie all the embedded elements together, and to control the overall flexibility of composite tube 1. FIG. 2 shows a cross section of composite tube 1, depicting the various layers forming the structure of the tube.

Elastomeric layer 20 is preferably formed of plastic having a pre determined flexural modulus. In general, the bending stiffness of a plastic tube can be determined from the formula:

$$K \sim (3*PI*E*t*d^3)/(8*l^3)$$

In the formula, E is the flexural modulus of the plastic, d is the tube diameter, $l$ is the tube length, and t is the tube thickness. According to the formula, the tube's bending stiffness is proportional to the cube of the tube diameter. As the tubes are made larger, it is then very important to use a plastic with a very low flexural modulus, otherwise the tube becomes too stiff to be useful in the medical applications envisioned. For example, for a tube having a diameter of about 20 mm, a plastic with a flexural modulus of no more than about 2000 PSI gives acceptable results. This value of the flexural modulus gives acceptable results for tubes used in endoscopy applications. However, other ranges of the flexural modulus can be preferred for other applications.

When the braid 10 is embedded in elastomeric layer 20 made of a plastic selected according to the considerations described above, additional care must be taken to combine the two elements so that the resulting composite element 40 obtains the desired properties. The plastic layer tends to increase the stiffness of the braid 10, so that the same torque can be transmitted by a smaller embedded braid as can be by a larger free braid. Accordingly, braid 10 can be thinner when embedded in elastomeric layer 20, resulting in an overall thinner wall of composite tube 1.

In addition, the open spaces between wires 12, 14 have to be kept relatively large. If those spaces are too small, the plastic that enters them when the braid 10 is embedded in elastomeric layer 20 binds the movement of the wires 12, 14, and excessively raises the stiffness of composite element 40. However, if sufficient space is left between the wires so that their relative motion is not prevented, the composite layer 40 can have improved properties over a braid alone. For example, a composite element 40 can be designed to transmit the same torque as a braid element 10 alone, but resulting in a thinner wall for tube 1. The braid spacing of braid 10 and the flexural modulus of the elastomeric layer 20 can thus be selected to obtain desired properties of composite element 40.

A coil 30 can also be included in composite tube 1. Coils can be easily stretched and compressed longitudinally, and are very flexible in bending, but tend to resist radial compression and expansion. One or more coils can thus be included in the construction of composite tube 1 to control the radial deformation of the braid 10. By placing a coil 30 radially inside of braid 10, radial movement of braid 10 is prevented towards the center of tube 1.

Figure 3:
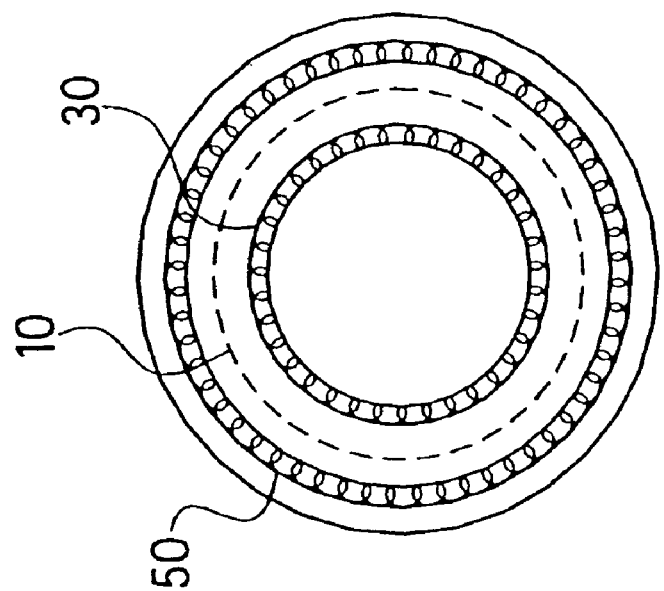
FIG. 3 is a cross section showing a second embodiment of a medical tube, with one braid and two coils.

As explained before, when a braid is stretched longitudinally its diameter is reduced. By placing coil 30 radially inward of braid 10, this radial contraction of braid 10 is prevented, so that braid 10 can better resist a tension force without deforming. Conversely, if a coil is placed radially outside of braid 10, radial expansion of braid 10 is prevented. Since the radius of the braid increases when it is compressed longitudinally, placing a coil outside of braid 10 opposes the longitudinal contraction, so that braid 10 can better withstand compressive forces. Coils can be placed both radially inside and outside of braid 10, to increase the braid's resistance to both compression and tension forces. For example, as shown in FIG. 3, an outer coil 50 can be placed radially outside braid 10. Outer coil 50 can also be either free or embedded in the elastomeric layer 20.

Coil 30 can also be used to increase the resistance to kinks of tube 1. When a tube kinks, its cross section collapses locally at the location of the kink. In other words, the diameter of the tube is reduced at the kink location, to the point that opposing tube surfaces may touch each other. Coil 30 prevents the radial collapse of braid 10 forming tube 1, so that the tube 1 does not kink easily. If coil 30 is selected to have a high stiffness, the tube 1 will be able to resist kinking more than if a coil 30 having a low stiffness is selected. However, selecting an excessively stiff coil 30 will tend to reduce too much the overall bending flexibility of tube 1. Coil stiffness is defined as the measure of the coil's resistance to bending and to radial compression.

Coil 30 can be, for example, formed of a round wire or of a flat wire. Flat wire coils are preferred, because they are thinner for a given strength, and permit construction of a thin walled tube. The coil can be embedded in elastomeric layer 20 similarly to braid 10, or can be a free coil. A tube with embedded coils can be more easily manufactured, for example by extrusion. However, embedding the coils can result in a tube excessively stiff in bending.

Composite tube 1 can also include an outer layer 80, shown in FIG. 2, that ensures the tube has a smooth and slippery outer surface, to facilitate travel within body cavities. A smooth layer 90 can also be used as an inner liner, so that medical tools placed in working channel 64 can travel easily along tube 1. Layers 80 and 90 can be formed, for example, of a silicone based material, or of a Teflon based material.

Figure 4:
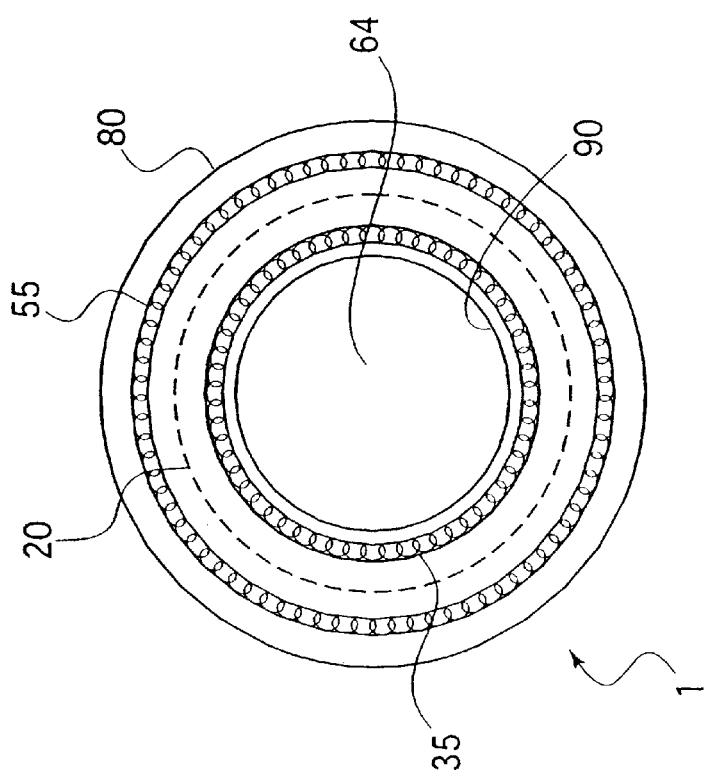
FIG. 4 is a cross section showing a third embodiment of a medical tube.

Several configurations of composite tube 1 have been developed in addition to the configurations shown in FIGS. 1–3. For example, when both inner and outer coils are used, the strengths of the coils can be tailored to obtain desired effects. As shown in FIG. 4, braid 20 is placed between an inner coil 35 and an outer coil 55. Inner coil 35 in this example is stronger and larger than outer coil 55. This design provides strong resistance to kinks and to tension loads, as explained above, and also provides some resistance to compression loads. The outer coil can be made less strong than the inner coil because compression resistance is generally limited by the column buckling of the long tube, rather than by the local resistance to compression of a section of the tube.

The two coils, in a preferred embodiment, provide sufficient rigidity to the structure that an elastomeric layer is not necessary. Accordingly, neither braid 20 nor coils 35, 55 have to be embedded in plastic. In one preferred embodiment, a smooth layer 90 is disposed on the radially inner surface of composite tube 1, so that medical tools inserted in working channel 64 are surrounded by a smooth surface.

Figure 5:
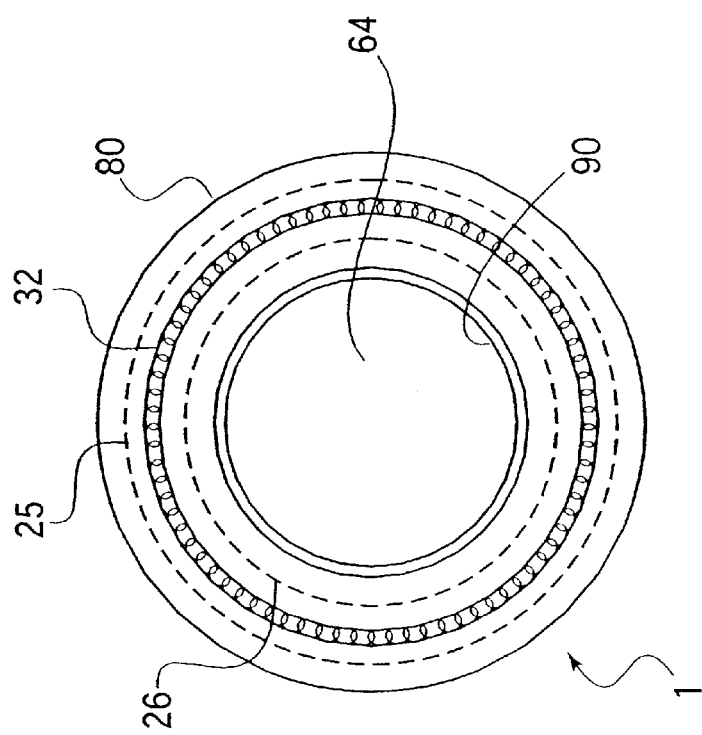
FIG. 5 is a cross section of a fourth embodiment of a medical tube.

Another preferred embodiment of the invention is shown in FIG. 5. In this embodiment, an inner braid 26 is placed adjacent to an inner surface of coil 32, and an outer braid 25 is placed adjacent to the outer surface of coil 32. In this manner, coil 32 cooperates with inner braid 26 to increase stiffness in compression of the composite tube, by preventing inner braid 26 from expanding radially. Coil 32 also increases the tensile stiffness of the composite tube, by preventing outer braid 25 from radially collapsing. Inner and outer coatings 80, 90 can be used to seal the assembly and provide smooth surfaces in a preferred embodiment, coil 32 can be a flat wire coil.

The embodiment shown in FIG. 5 is especially well suited for use as a sheath for colonoscopes. In this application, composite tube 1 travels to the cecum and provides a channel in which additional medical tools can be inserted. The invention is well suited for this application, that requires great flexibility in bending, with high rigidity in torsion, compression and tension. The embodiments shown in FIGS. 4 and 5 are also especially well suited for incorporation in a GERD tube device. However, these embodiments can also be used in the other applications earlier described.

The composite tube according to the invention can be manufactured using various known techniques. For example, the desired configuration of coils and braids can be assembled on a cylindrical core, and then the assembly can be heated and dipped in molten plastic, to coat the components. The coated assembly can then be cured in an oven. This technique is simple, and provides smooth inner and outer surfaces. However, the braid does not generally become completely embedded in the plastic, and the wall thickness of the resulting tube is not uniform.

Another technique for manufacturing the composite tube is to place the braid on a core, and then extrude a layer of plastic with the braid. After cooling and stabilizing the plastic, the coils can be added to the assembly. This method is more labor intensive, but produces more consistent wall thicknesses, and fully embedded braids.

A heat shrink layer can also be used to make the composite tube. For example, the braid and coil can be assembled, and various tube shaped plastic layers, including a heat shrink layer, can be placed on the assembly. The assembly is heated, and the plastic layers melt and shrink on the braid and coils, as desired. The specific details of manufacturing can be selected to obtain specific properties of the composite tube.

It will be apparent to those skilled in the art that various modifications and variations can be made in the structure and the methodology of the present invention, without departing from the spirit or scope of the invention. Thus, it is intended that the present invention cover the modifications and variations of this invention provided they come within the scope of the appended claims and their equivalents.

What is claimed is:

1. A flexible composite tube for medical applications having a longitudinal axis, comprising:
   a tubular braid adapted to transfer a torque along the longitudinal axis, wherein the tubular braid is made of intertwined wire elements and extends as a substantially continuous tube along the longitudinal axis;
   at least one coil disposed longitudinally along the tube, adapted to limit radial movement of the tubular braid, wherein said at least one coil is not interwoven with any other coil and is disposed radially inward of the tubular braid;
   a second coil disposed radially outward of the tubular braid, wherein the second coil has lower stiffness than the coil disposed radially inward of the tubular braid; and
   a tube-shaped elastic layer, wherein the tubular braid is embedded in the elastic layer, the tube-like elastic layer forming a composite element with the tubular braid to restrict relative movement of the wire elements.

2. A flexible composite tube for medical applications having a longitudinal axis, comprising:
   a tubular braid adapted to transfer a torque along the longitudinal axis, wherein the tubular braid is made of intertwined wire elements;
   a first coil adapted to limit radial movement of the tubular braid, wherein the first coil is disposed longitudinally along the tube and disposed radially inward of the tubular braid;
   a second coil disposed radially outward of the tubular braid, wherein the second coil has lower stiffness than the first coil; and
   a tube-shaped elastic layer, disposed adjacent the tubular braid, forming a composite element with the tubular braid to restrict relative movement of the wire elements.

3. The tube according to claim 2, further comprising an outer smooth coating disposed radially outward of the second coil and of the composite element.

* * * * *